United States Patent [19]

Bernon

[11] Patent Number: 5,207,687
[45] Date of Patent: May 4, 1993

[54] APPARATUS FOR EXTRACTING A FETUS THROUGH THE NATURAL GENITAL TRACT OF THE MOTHER

[76] Inventor: Gilles Bernon, 24, rue Pierre-Mendes-France, F-77200 Torcy, France

[21] Appl. No.: 635,538
[22] PCT Filed: May 26, 1989
[86] PCT No.: PCT/FR89/00252
 § 371 Date: Jan. 16, 1991
 § 102(e) Date: Jan. 16, 1991
[87] PCT Pub. No.: WO89/11253
 PCT Pub. Date: Nov. 30, 1989

[30] Foreign Application Priority Data

May 26, 1988 [FR] France .................. 88 07004

[51] Int. Cl.⁵ ......................................... A61B 17/42
[52] U.S. Cl. ...................... 606/122; 56/332; 606/119
[58] Field of Search ............. 606/119–124; 56/329, 332

[56] References Cited

U.S. PATENT DOCUMENTS

| | | | |
|---|---|---|---|
| 13,453 | 8/1855 | Buffum | 606/122 |
| 705,141 | 7/1902 | Rauch | 56/332 |
| 713,166 | 11/1902 | St. Cyr | 606/122 |
| 771,842 | 10/1904 | Stansbury et al. | 56/332 |
| 2,792,838 | 5/1957 | Guerriero | 606/122 |
| 4,597,391 | 7/1986 | Janko | 606/122 |
| 4,875,482 | 10/1989 | Hariri et al. | 606/122 |

Primary Examiner—Peter A. Aschenbrenner
Attorney, Agent, or Firm—Oblon, Spivak, McClelland, Maier & Neustadt

[57] ABSTRACT

The apparatus comprises a carcass which includes a plurality of flexible rods arranged substantially as a corolla, and which are integral at one of their ends with a tubular hollow sleeve and at their opposite free ends with a crosslinked structure made of flexible material extending insider the corolla and of which the bottom is made integral with an appropriate traction member. The apparatus is designed for difficult deliveries of babies.

6 Claims, 2 Drawing Sheets

APPARATUS FOR EXTRACTING A FETUS THROUGH THE NATURAL GENITAL TRACT OF THE MOTHER

TECHNICAL FIELD

The present invention relates to an instrument for extracting a fetus through the natural genital tract, that is to say through the vaginal tract.

BACKGROUND ART

Three types of instrument are presently available intended to grasp the head of a fetus in order to extract it from the natural genital tract of the mother, with the aim of shortening the period of delivery in cases of fetal distress or an arrest in the descent of the fetus head. These instruments are the forceps, the vacuum extractor and the spatulas.

As is known, the forceps is a pincer with two arms which is said to date from Roman times, but whose modern forms date from the 16th century. There are forceps with crossed arms and forceps with parallel arms. The forceps which have crossed arms, articulated on each other, and in which the "jaws" or "spoons" of the pincer present a cephalic curvature adapting to the fetus head and a pelvic curvature adapting to the pelvic floor of the mother, comprise means for pulling on the spoons, the best adapted of these means being those included in the TARNIER forceps.

The forceps with parallel arms developed by DEMELIN eliminates the problems of articulation caused by the forceps with crossed arms. In this second type of forceps, the uncrossed arms, articulated by means of a screw, at the level of the handles extending the spoons, which can be tightened as desired, thus protecting the fetus head, have been replaced by forceps with parallel arms which are made integral by means of a transverse arm and on which cords can be attached.

It should be noted that in 1860 CHASSAGNY had suggested attaching cords to arms carried by the spoons in forceps with crossed arms, and intended to permit the application of traction forces on the spoons in the proximity of the fetus head; however, these cords were unable to observe the pelvic curvature, so that this forceps was quickly abandoned to the benefit of the TARNIER forceps.

It was in 1950 that the THIERRY spatulas were proposed, which consist of two completely independent spoons and which do not therefore constitute a pincer. These two symmetrical spatulas comprise a solid spoon with a facial curvature and pelvic curvature, and a rectilinear handle having at its free end notches for receiving the fingers of the obstetrician; their purpose is to simulate, in the fetus head, movements similar to the physiological movements, but while at the same time respecting its mobility.

The obstetric vacuum extractors for extracting a fetus are made up of three main elements: a gripping system, a pulling device and a vacuum generator.

The gripping system is made up of a cup, or metallic extractor, of a diameter suitable for providing a sufficient adherence. The pulling device is made up of a metal plate held at a slight distance from the extractor and in whose center there is attached a small metal chain which passes through the inside of a flexible rubber tube itself connected to the outer orifice of the extractor and at the opposite end of which there is fitted a cruciform metal handle, one of the hollow branches of which permits the introduction of a rod engaging the pulling chain. The vacuum generator is made up of a vacuum pump provided with a manometer and functioning by hand.

In order to prevent the possible traumatic effects of the metal instruments, flexible systems such as tapes, slings or nets have been proposed for fetus extraction, particularly in Japan in the 18th century; among these, a pliable whalebone collar intended to be passed round the end of the fetus and connected at its opposite end to a wooden handle used for pulling; a piece of silk connected to a silk tape for pulling.

The obstetric extractor by Dr. John EVANS (CHICAGO, middle of 19th century) is also known, this being made up of two parallel steel arms with a curve for following the bottom of the sacrum and a joint permitting relative mobility near the end of the curved segment, while the parallel bars were held together by means of a flat clasp, on the handles, during the introduction of the curved ends into the pelvis; a net of silk tape intended to surround the fetus head was fixed to the curved end arms. Following introduction, the clasp was removed, the arms were separated and one of them was passed by way of the opposite side of the pelvis, in such a way as to encircle the fetus head in the net. With the aid of the long tapes of the net, which hung from the vagina, the obstetrician exerted a pull alternately on each of their attached ends and on the steel arms in order to bring about the descent of the fetus head. The efficiency of this type of extractor with parallel arms, without any transverse arm or articulation screw has not been demonstrated, and so it has not gained recognition in practice.

There has also been proposed, in German Patent Application HEEGE No. 2,233,840, an obstetric apparatus which comprises a crosslinked tube whose front part is provided with a dilatable edge, this tube being arranged in a gripping sleeve and being capable of being widened at least as far as the size of a neonate's head using flexible guide rods which are mounted displaceably in said sleeve and are attached to the abovementioned edge.

DISCLOSURE OF THE INVENTION

However, the obstetrics apparatus according to this patent application presents considerable risks for a neonate: the dilatable edge and the marginal zone adjacent to this edge can in fact be contracted using a lace surrounded by said edge, after the crosslinked tube has been positioned on the head of the neonate, this contraction being such that the head is completely enveloped by said tube. Now, the lace, together with the edge to which it is joined, constitutes a risk of strangulation of the neonate.

The instruments presently in use for extracting the fetus head present a certain number of disadvantages: they must be used by obstetricians skilled in their handling in order to avoid any resulting injury to the baby and/or the mother, results which they are not however always in a position to avoid, because of the rigid metal structure of the instruments used and their working principle.

The object of the present invention is consequently to provide an apparatus for extracting fetuses, particularly human fetuses, through the natural genital tract of the mother, which apparatus better satisfies the practical requirements than do the instruments proposed in the prior art, in that it ensures a better gripping of the fetus head without risk of trauma both to the mother and the baby, in that it avoids any friction by insulating the head of the fetus, in its descent movement, from the soft parts of the pelvis, and in that its design is such that it can be made at a cost which is sufficiently low to warrant its "one-off" use, thereby avoiding the sterilization operations to which these sorts of instruments are usually subjected.

The present invention relates to an apparatus for extracting a fetus through the natural genital tract of the mother, comprising a body consisting of a plurality of flexible rods arranged substantially as a corolla, and which are integral at one of their ends with a crosslinked structure made of flexible material, said structure extending inside the abovementioned corolla, and a tubular hollow sleeve, wherein said rods are integral at their opposite ends with the tubular sleeve, said crosslinked structure made of flexible material is made up of two networks imbricated one in the other, of which one is a closed-mesh network and the other is a free-mesh network, the braids of which make up the free-mesh network comprising at their end, which extends freely inside the abovementioned corolla, traction strands fixed to said end, and which terminate at their opposite ends in an anchoring core capable of being received in a suitable traction member.

According to an advantageous embodiment of the apparatus according to the present invention, the traction strands are guided in the abovementioned tubular sleeve.

According to another advantageous embodiment of the apparatus according to the present invention, the traction member comprises a cage intended to receive the abovementioned anchoring core, on a part of which cage there is mounted a movable sleeve tube, and whose end opposite that on which the sleeve tube is mounted bears a traction handle.

According to an advantageous arrangement of this embodiment, the sleeve tube is mounted so as to be movable on the end part of the anchoring cage oriented toward the tubular hollow sleeve of the extraction apparatus.

According to an advantageous form of this arrangement, said end part is provided with a thread corresponding to the internal thread with which the abovementioned sleeve tube is also provided.

According to another advantageous embodiment of the abovementioned traction member, the sleeve tube cooperates with a stop integral with the abovementioned tubular hollow sleeve.

In addition to the above arrangements, the invention furthermore comprises other arrangements, which will emerge from the description which follows.

BRIEF DESCRIPTION OF THE DRAWINGS

The invention will be better understood with the aid of the remaining description which follows and in which reference is made to the attached drawings in which.

BEST MODE FOR CARRYING OUT THE INVENTION

Figure 1:
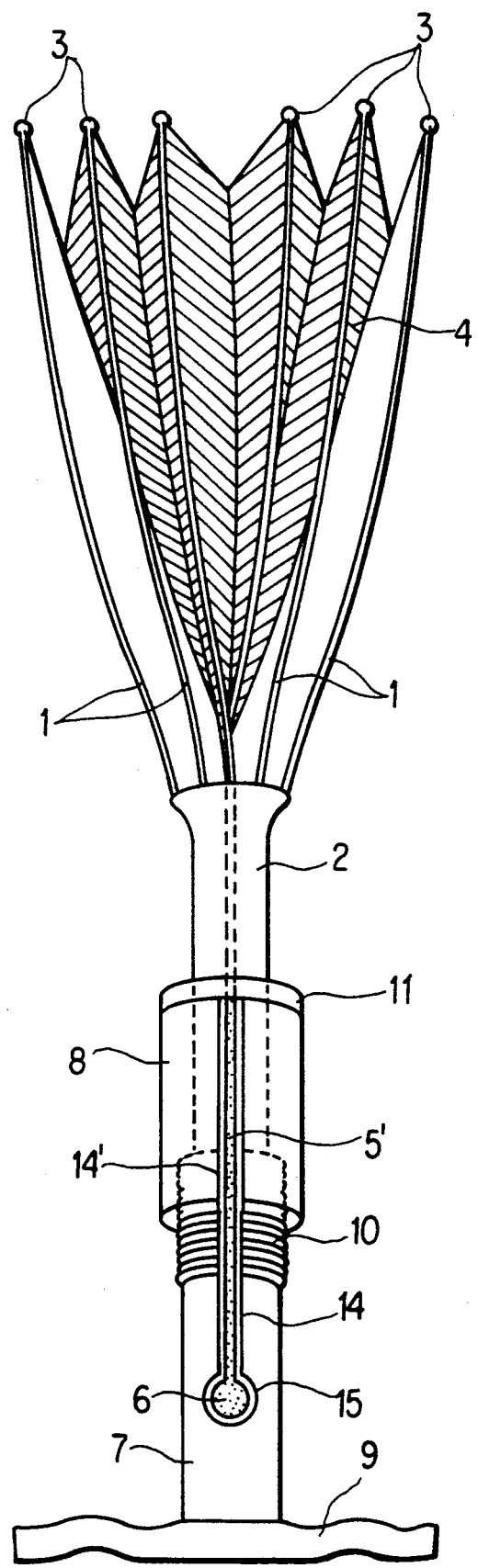
FIG. 1 is a side elevational view of an apparatus for extracting the fetus head, in accordance with the present invention.

It should be understood, however, that these drawings and the corresponding descriptive sections are given solely by way of illustration of the object of the invention, and they do not in any way constitute a limitation thereon.

The apparatus for expelling the fetus through the natural genital tract of the mother, in accordance with the present invention, comprises a plurality of rods 1 made of a suitable material conferring upon them a certain resiliency: metal, plastic material, etc. These rods 1 are fixed at one of their ends to a hollow tubular sleeve 2, while, at their free ends 3, there is fixed a crosslinked structure 4 which extends inside the structure substantially as a corolla defined by the union of the rods 1 made integral, at their lower ends, with said sleeve 2. The dimensions of the crosslinked structure 4 are sufficient to allow it to enclose the head of the fetus during operations for extracting the fetus.

Traction strands 5 are fixed to the lower part of the crosslinked structure 4 and are guided in the sleeve 2. It is the traction of these strands 5 which permits the functioning of the apparatus according to the invention and the expulsion of the fetus.

These strands 5 are advantageously united in a cord 5' which ends in an anchoring core 6, which is capable of being received in the anchoring cage 7 of a removable traction member. Said traction member comprises, in addition to said anchoring cage 7, a sleeve tube 8 and a traction handle 9. The sleeve tube 8 is mounted movably on the end part 10 of the anchoring cage 7 oriented in the direction of the abovementioned sleeve 2; the sleeve tube 8 is given mobility by providing the end part 10 of the anchoring cage 7 with a thread which cooperates with a corresponding internal thread with which the sleeve tube 8 is provided. The traction handle 9 is fixed to the end of the anchoring cage 7 opposite that one which bears the thread 10. Movement of the sleeve tube is limited by the arrangement of a stop collar 11 fixed on the sleeve 2.

The traction member is easy to connect to the actual expulsion apparatus which is made up of the corolla 1, the crosslinked structure 4 with the traction strands 5 and the sleeve-handle 2.

Figure 2:
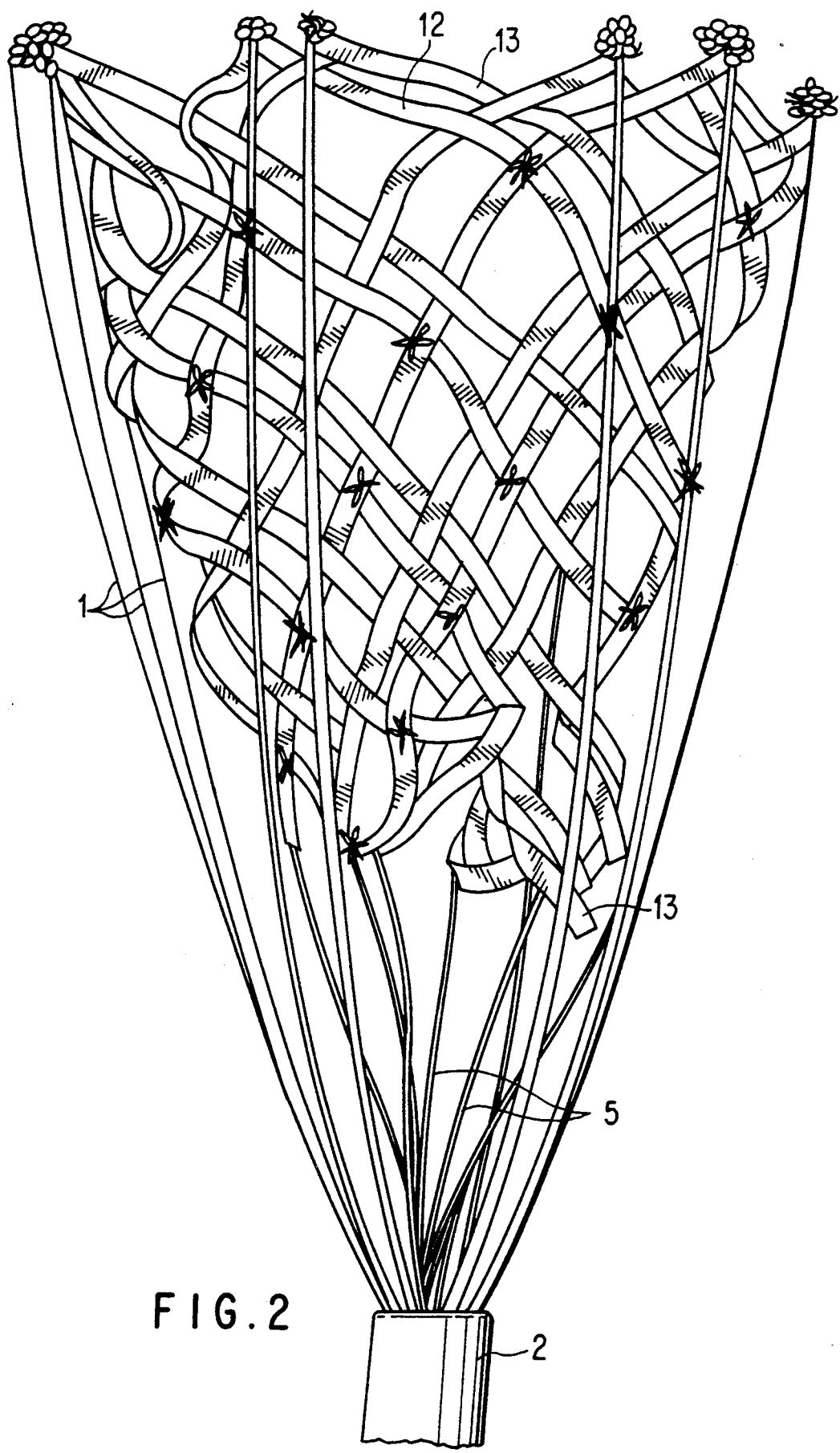
FIG. 2 is a view, on a larger scale, of the flexible crosslinked structure and of the semirigid corolla to which it is attached at one of its ends.

The crosslinked structure, made of a flexible material, consists of two networks closely imbricated one in the other, of which one has closed or interconnected meshes 12 and of which the other is made up of a free-mesh network 13 which includes separate meshes which are not interconnected, as shown in FIG. 2. The braids which form the network 12 and the network 13 are fixed together at each of the free ends of the rods 1 which form the abovementioned corolla, and the crosslinked structure 4, made up of these two linked networks 12 and 13, extends inside said corolla. Whereas the braids of the two networks are fixed to the free ends of the rods 1 of the corolla, only the braids of the free-mesh network 13 are connected, in a non-removable manner, with the traction strands 5.

The flexible material of which the crosslinked structure 4 is made is advantageously, but not restrictively, of a suitable textile material or a synthetic material or even a suitable flexible material.

The rods 1 are advantageously, but not restrictively, made up of metal wires which are preferably semi-rigid and afford a certain resiliency, or of wires made of plastic material satisfying the same criteria. It is advantageous to cover said rods 1 with a material facilitating the sliding of the apparatus inside the genital tract of the mother, such as TEFLON in particular.

The functioning of the apparatus for fetal extraction according to the present invention is as follows:

When the conditions for the expulsion stage are combined and it is desired to shorten the fetal distress and/or the expulsion efforts or to remedy the arrest or absence of the expulsion efforts, recourse is made to the assistance of the fetal expulsion apparatus according to the present invention, by proceeding as follows:

The "applicator" part of the apparatus, which comprises the corolla 1 on which is fixed the crosslinked structure 4 maneuvered by the traction strands and which is itself fixed to the sleeve 2 via the lower ends of the rods 1 which it comprises, is introduced through the genital tract of the mother until contact is made with the fetus head, while exerting a slight traction on the traction strands, preferably combined in a cord 5', in order to reduce the diameter of the applicator. The traction exerted on the cord 5' is then relaxed, and the rods 1 are engaged around the fetus head. The traction member (which consists of the sleeve tube 8, the anchoring cage 7 and the traction handle 9) is then connected to the sleeve-handle 2 of the applicator, while simultaneously introducing the traction cord 5' and the anchoring core 6 into the anchoring cage 7, then the sleeve tube 8 is screwed on the thread 10 of the anchoring cage 7 and is brought into contact with the stop collar 11 mounted on the sleeve-handle 2 of the applicator.

As illustrated in FIG. 1, anchoring core 6 engages a recess 15 formed in anchorage cage 7. Cords 5' are positioned in a groove 14' formed in sleeve 8 and in a groove 14 formed in anchoring cage 7 and are connected to the free mesh network 13 as previously described and as shown in FIG. 2. A wall portion of recess 15 is shown in FIG. 1 and serves to apply a force on anchoring core 6 when anchoring cage 7 is unscrewed from sleeve tube 8. This, in turn, exerts a traction force on the traction cords 5' of traction strand 5, which also then exerts a pulling force on free mesh network 13 and correspondingly a pulling force on the free ends 3 of rods 1 which bends the rods radially inward.

The force exerted by the sleeve tube 8 on the stop 11 results in the convex curvature of the rods 1 which form the abovementioned corolla, which rods exert a slight weight on the soft parts of the pelvis, sufficient to distance them from the head of the fetus and to facilitate its descent by distancing the obstacles from it; at the same time as said convex curvature of the rods 1 is obtained, by virtue of the fact that it is integral with the free ends of the rods 1 of the corolla, the crosslinked structure 4 tightens around the fetus head, around which it forms a nontraumatic gripping net. The expulsion is then effected by acting on the traction handle 9. As can be appreciated from FIG. 2, the free mesh network 13, when pulled by the traction cords, cause the free ends 3 of the rods, due to their resulting convex curvature, to bend radially inward to surround the head of the fetus and the head is simultaneously surrounded by the closed or interconnected meshes 12.

An expulsion is thereby obtained without risks of trauma both to the mother and to the baby.

Indeed, the adjustable convexity of the rods 1, whose free ends can advantageously be spatulate, opens the passage for the fetus head in its descent, while isolating it from the soft parts of the pelvis, thereby avoiding any friction; the flexible material used to make the crosslinked structure 1 and the distribution of the pressure forces over a surface area of the fetal cranium which is greater than that permitted by the expulsion apparatuses of the prior art provide for improved non-traumatic gripping. In addition, the small thickness of the rods 1 and their advantageously spatulate ends, as well as their ease of sliding by virtue of the provision of a suitable covering, permit a straightforward introduction into the space around the fetus head at the level of the pelvic cavity.

By virtue of its design, the extraction apparatus according to the present invention has the additional advantage that it can be made on an industrial scale at a relatively low cost, allowing the "applicator" part of the apparatus to be designed as a one-off use instrument, the traction member for its part being re-usable.

Such a design makes it possible to use an instrument sterilized at the end of manufacture and supplied in sterile packaging, and to thereby avoid the sterilization operations at hospital level which are relatively long and require monitoring on the part of the hospital staff.

As emerges from the above, the invention is not in any way limited to those of its embodiments and applications which have just been described in detail; on the contrary, it embraces all variants thereof which may occur to the person skilled in the art, without departing from the framework or from the scope of the present invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for extracting a fetus through the natural genital tract of the mother, which comprises: a tubular sleeve and a body having a plurality of flexible rods arranged substantially as a corolla, said rods being connected at one of their ends with said tubular hollow sleeve and at a free opposite end with a crosslinked structure made of flexible material, extending inside said corolla; and a base connected with a traction member, wherein said crosslinked structure comprises two networks imbricated one in the other, of which one is a closed-mesh network and the other is a free-mesh network having braids, said braids including at ends thereof which extend inside said corolla, wherein traction strands are fixed to said ends, and wherein said traction strands terminate at an opposite end fixed to the crosslinked structure in an anchoring core positioned in said traction member.

2. The apparatus as claimed in claim 1, which comprises guide means for guiding said traction strands in said tubular sleeve.

3. The apparatus as claimed in claims 1 or 2, wherein the traction member comprises a cage member for receiving said anchoring core, a movable sleeve tube is mounted on said cage, and wherein a traction handle is connected to an end portion of said anchoring cage.

4. The apparatus as claimed in claim 3, wherein the sleeve tube is movably mounted to an end portion of the anchoring cage.

5. The apparatus as claimed in claim 4, wherein said end portion is provided with a threaded portion corresponding to the initial internal thread portion of said sleeve tube.

6. The apparatus as claimed in claim 3, wherein said sleeve includes a stop member and wherein the sleeve engages said stop of said sleeve.

* * * * *